United States Patent [19]

Ramanathan et al.

[11] Patent Number: 5,714,371
[45] Date of Patent: Feb. 3, 1998

[54] METHOD FOR REFOLDING INSOLUBLE AGGREGATES OF HEPATITIS C VIRUS PROTEASE

[75] Inventors: Lata Ramanathan, West Orange; Michele Wendel, Fanwood, both of N.J.

[73] Assignee: Schering Corporation, Kenilworth, N.J.

[21] Appl. No.: 571,643

[22] Filed: Dec. 13, 1995

Related U.S. Application Data

[63] Continuation-in-part of Ser. No. 439,680, May 12, 1995, abandoned.
[51] Int. Cl.$^6$ .............................. C12N 9/50; C12P 21/06; C07K 1/00
[52] U.S. Cl. .......................... 435/219; 435/69.1; 530/427
[58] Field of Search .................................. 435/219, 69.1, 435/814; 530/427

[56] References Cited

U.S. PATENT DOCUMENTS

| | | | |
|---|---|---|---|
| 4,620,948 | 11/1986 | Builder et al. | 530/419 |
| 4,929,700 | 5/1990 | Halenbeck et al. | 530/351 |
| 4,931,543 | 6/1990 | Halenbeck et al. | 530/351 |
| 4,977,248 | 12/1990 | Creighton et al. | 530/412 |
| 5,162,507 | 11/1992 | Wolfe et al. | 530/412 |

FOREIGN PATENT DOCUMENTS

| | | |
|---|---|---|
| 433225 | 6/1991 | European Pat. Off. |

OTHER PUBLICATIONS

N.B. Cited references were provided with copending application 08/439,680.

Primary Examiner—Michael G. Wityshyn
Assistant Examiner—Jon P. Weber
Attorney, Agent, or Firm—Jaye P. McLaughlin; Norman C. Dulak

[57] ABSTRACT

A method for solubulizing and refolding insoluble aggregates of HCV protease is presented. Insoluble aggregates of HCV NS3 protease are extracted from bacteria producing the aggregates. The aggregates of HCV NS3 are then solubilized in a buffer containing the denaturing reagent. Solubilized protease is then placed in an acidic buffer containing a reducing agent. The denaturing reagent is then removed from the buffer under acidic conditions. The pH of the buffer containing HCV NS3 protease is then raised in a step-wise manner to a pH of about 7–8 so as to produce properly refolded soluble, active HCV NS3 protease.

12 Claims, 4 Drawing Sheets

METHOD FOR REFOLDING INSOLUBLE AGGREGATES OF HEPATITIS C VIRUS PROTEASE

This is a continuation-in-part application of U.S. patent application Ser. No. 08/439,680, filed May 12, 1995, now abandoned.

BACKGROUND OF THE INVENTION

Hepatitis C virus (HCV) is considered to be the major etiological agent of non-A non-B (NANB) hepatitis, chronic liver disease, and hepatocellular carcinoma (HCC) around the world. The viral infection accounts for greater than 90% of transfusion -associated hepatitis in U.S. and it is the predominant form of hepatitis in the adults over 40 years of age. Almost all of the infections result in chronic hepatitis and nearly 20% of people infected develop liver cirrhosis.

The virus particle has not been identified due to the lack of an efficient in vitro replication system and the extremely low amount of HCV particles in infected liver tissues or blood. However, molecular cloning of the viral genome has been accomplished by isolating the messenger RNA (mRNA) from the serum of infected chimpanzees then cloned using recombinant methodologies. [Grakoui A. et al. *J. Virol.* 67: 1385–1395 (1993)] It is now known that HCV contains a positive strand RNA genome comprising approximately 9400 nucleotides, whose organization is similar to that of flaviviruses and pestiviruses. The genome of HCV, like that of flavi- and pestiviruses, encodes a single large polyprotein of about 3000 amino acids which undergoes proteolysis to form mature viral proteins in infected cells.

Figure 1:
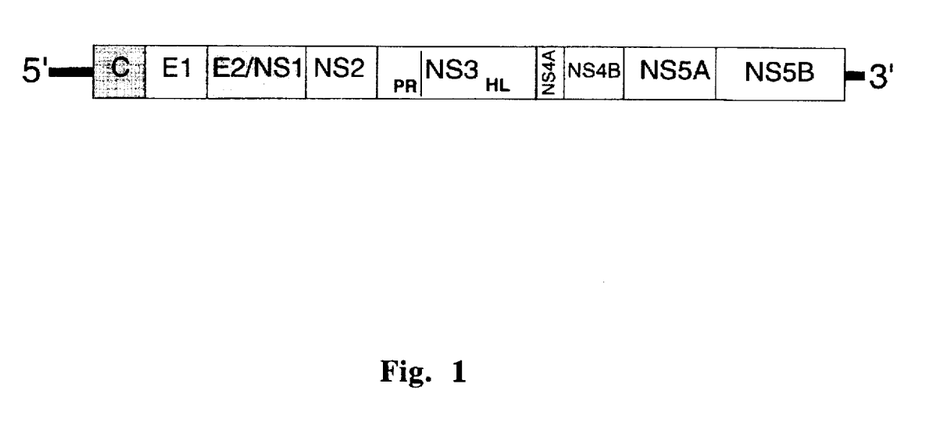
FIG. 1 schematically depicts the HCV polyprotein.

Cell-free translation of the viral polyprotein and cell culture expression studies have established that the HCV polyprotein is processed by cellular and viral proteases to produce the putative structural and nonstructural (NS) proteins. At least nine mature viral proteins are produced from the polyprotein by specific proteolysis. The order and nomenclature of the cleavage products are as follows: $NH_2$-C-E1-E2-NS2-NS3-NS4A-NS4B-NS5A-NS5B-COOH. (FIG. 1). The three amino terminal putative structural proteins, C (capsid), E1, and E2 ( two envelope glycoproteins), are believed to be cleaved by host signal peptidases of the endoplasmic reticulum(ER). The host enzyme is also responsible for generating the amino terminus of NS2. The proteolytic processing of the nonstructural proteins are carried out by the viral proteases: NS2-3 and NS3, contained within the viral polyprotein. The NS2-3 protease catalyzes the cleavage between NS2 and NS3. It is a metalloprotease and requires both NS2 and the protease domain of NS3. The NS3 protease catalyzes the rest of the cleavages of the substrates in the nonstructural part of the polyprotein. The NS3 protein contains 631 amino acid residues and is comprised of two enzymatic domains: the protease domain contained within amino acid residues 1–181 and a helicase ATPase domain contained within the rest of the protein. It is not known if the 70 kD NS3 protein is cleaved further in infected cells to separate the protease domain from the helicase domain, however, no cleavage has been observed in cell culture expression studies.

The NS3 protease is a member of the serine class of enzymes. It contains His, Asp, and Ser as the catalytic triad, Ser being the active site residue. Mutation of the Ser residue abolishes the cleavages at substrates NS3/4A, NS4A/4B, NS4B/5A, and NS5A/5B. The cleavage between NS3 and NS4A is intramolecular, whereas the cleavages at NS 4A/4B, 4B/5A, 5A/5B sites occur in trans.

Experiments using transient expression of various forms of HCV NS polyproteins in mammalian cells have established that the NS3 serine protease is necessary but not sufficient for efficient processing of all these cleavages. Like flaviviruses, the HCV NS3 protease also requires a cofactor to catalyze some of these cleavage reactions. In addition to the serine protease NS3, the NS4A protein is absolutely required for the cleavage of the substrate at the 4B/5A site and increases the efficiency of cleavage of the substrate between 5A/5B, and possibly 4A/4B.

Because the HCV NS3 protease cleaves the non-structural HCV proteins which are necessary for the HCV replication, the NS3 protease can be a target for the development of therapeutic agents against the HCV virus. The gene encoding the HCV NS3 protein has been cloned as disclosed in U.S. Pat. No. 5,371,017, however, not in a soluble active form. If the HCV protease is to be useful as a target in a screen to discover therapeutic agents, the protease must be produced in a soluble active form. Thus, there is a need for a soluble active form of the HCV protease which can be produced in large quantities to be used in a high throughput screen to detect inhibitors of the protease and for structural studies. We have cloned and expressed the catalytic domain of NS3 protease as a native protein and as fusion proteins in *E. coli* and in Yeast. Fusion tags were used to facilitate purification and secretion into periplasmic space. All of these constructions resulted in expression of NS3 protein only in insoluble form. Various attempts which include growing bacteria in different media and temperatures, expressing in different strains of *E. coli* failed to produce expression of soluble NS3. Thus, there is a need for a soluble active form of the HCV protease which can be used in a screen to test for potential therapeutic agents.

SUMMARY OF THE INVENTION

The present invention fills this need by providing for a process for producing soluble, proteolytically active, refolded HCV protease from insoluble, bacterially produced HCV protease aggregates. Insoluble, aggregates of HCV NS3 protease are extracted from bacteria producing said aggregates. The aggregates of protease are then solubilized in a buffer containing a denaturing reagent. The solubilized protease is then placed in a buffer containing a reducing agent said buffer having an acidic pH. The denaturing reagent is then removed from the buffer under conditions wherein the buffer maintains an acidic pH. The pH of the buffer containing the protease is then raised in a stepwise manner to a pH of about 7–8 so as to produce properly refolded soluble, active HCV NS3 protease.

In a preferred embodiment of the present invention, the insoluble protease is first extracted from the bacteria by homogenization or sonication of the bacteria. The aggregates containing the HCV protease are then solubilized in a 5M solution of guanidine hydrochloride (GuHCl). The NS3 protease is then purified from high molecular weight aggregates by size exclusion chromatography, as for example by applying the solution to a SEPHACRYL S-300 size exclusion gel chromatography. Fractions containing the NS3 protease are collected and the solution comprised of 5M solution of GuHCl is diluted to about 0.1M GuHCl in a refolding buffer containing dithiothreitol and lauryl maltoside. The diluted solution is then applied to a reverse phase chromatography column and pools containing the NS3 protease collected. The pH of the protease fractions is then raised in a stepwise manner to about 7.4–7.8 so as to produce properly refolded soluble, active NS3 protease.

DETAILED DESCRIPTION OF THE INVENTION

The teachings of all references cited are incorporated herein in their entirety by reference.

The amino acid sequence of the NS3 protease catalytic domain is shown in SEQ ID NO: 1. Prior to the present invention the NS3 protease could not be produced in a soluble form in sufficient quantities for extraction and purification. The present invention provides for a method to solubilize and refold bacterially produced soluble HCV protease.

According to the present invention, soluble HCV NS3 protease can be produced having the sequences shown in SEQ ID NO: 1 and SEQ ID NO: 2. The NS3 protease can also have a histidine tag fused to its amino acid terminus for use in purifying the protein on a nickel ($Ni^{2+}$) coated resin. See SEQ ID NO: 4. The protease is produced as insoluble aggregates, i.e. inclusion bodies, in bacteria such as E. coli.

The insoluble HCV NS3 protease is first extracted from the bacteria by homogenization or sonication of the bacteria. The aggregates containing the HCV NS3 protease are then solubilized in a solubilizing agent. Suitable solubilizing agents are guanidine hydrochloride (GuHCl), urea and glutothiocyanate. Preferably the solubilizing agent is a 5M solution of GuHCl. In a preferred embodiment, the solubilized NS3 protease is then purified from high molecular weight aggregates by size exclusion chromatography, as for example by applying the solution to a SEPHACRYL S-300 size exclusion gel column. Fractions containing the NS3 protease in the solubilizing agent are diluted in a refolding buffer containing a reducing agent. Examples of suitable reducing agents are dithiothreitol (DTT), dithioerythritol (DET) and β-mercaptoethanol. The preferred refolding buffer contains about 10% DTT. The refolding buffer also preferably contains a non-ionic detergent. Examples of non-ionic detergents are lauryl maltoside, a polyoxyethylene ether such as TRITON X-100®, Nonidet P-40®, a polyoxyethylene 9-lauryl ether such as THESIT®, (3-[(3-Cholamidopropyl)-dimethylammonio]-1-propanesulfonate) (CHAPS), and octylglucoside. Preferably the insoluble aggregates of protease are solubilized in 5M GuHCl. Purified fractions from a size exclusion gel column are pooled and diluted to about 0.1M GuHCl in a refolding buffer comprised of 10% dithiothreitol and 0.1% lauryl maltoside. The diluted solution is then applied to a reverse phase chromatography column and pools containing the NS3 protease collected. The pH of the protease fractions is then raised in a stepwise manner to about 7–8, preferably 7.4–7.8, so as to produce properly refolded soluble, active NS3 protease.

DNA encoding the NS3 protease of this invention can be prepared by chemical synthesis using the known nucleic acid sequence [Ratner et al., Nucleic Acids Res. 13:5007 (1985)] and standard methods such as the phosphoramidite solid support method of Matteucci et al. [J Am. Chem. Soc. 103:3185 (1981)] or the method of Yoo et al. [J. Biol. Chem. 764:17078 (1989)]. See also Glick, Bernard R. and Pasternak, *Molecular Biotechnology:* pages 55–63, (ASM Press, Washington, D.C. 1994). The gene encoding the protease can also be obtained using the plasmid disclosed in Grakoui, A., Wychowski, C., Lin, C., Feinstone, S. M., and Rice, C. M., Expression and Identification of Hepatitis C Virus polyprotein Cleavage Products, *J. Virol* 67;1385–1395 (1993). Also, the nucleic acid encoding HCV protease can be isolated, amplified and cloned (from patients infected with the HCV virus). Furthermore, the HCV genome has been disclosed in PCT WO 89/04669 and is available from the American Type Culture Collection (ATCC), 12301 Parklawn Drive, Rockville, Md. under ATCC accession no. 40394.

Of course, because of the degeneracy of the genetic code, there are many functionally equivalent nucleic acid sequences that can encode mature human HCV protease as defined herein. Such functionally equivalent sequences, which can readily be prepared using known methods such as chemical synthesis, PCR employing modified primers and site-directed mutagenesis, are within the scope of this invention.

As used herein, the term "transformed bacteria" means bacteria that have been genetically engineered to produce a mammalian protein. Such genetic engineering usually entails the introduction of an expression vector into a bacterium. The expression vector is capable of autonomous replication and protein expression relative to genes in the bacterial genome. Construction of bacterial expression vectors is well known in the art, provided the nucleotide sequence encoding a desired protein is known or otherwise available. For example, DeBoer in U.S. Pat. No. 4,551,433 discloses promoters for use in bacterial expression vectors; Goeddel et al. in U.S. Pat. No. 4,601,980 and Riggs, in U.S. Pat. No. 4,431,739 disclose the production of mammalian proteins by *E. coli* expression systems; and Riggs supra, Ferretti et al. *Proc. Natl. Acad. Sci.* 83:599 (1986), Sproat et al., *Nucleic Acid Research* 13:2959 (1985) and Mullenbach et al., *J. Biol. Chem* 261:719 (1986) disclose how to construct synthetic genes for expression in bacteria. Many bacterial expression vectors are available commercially and through the American Type Culture Collection (ATCC), Rockville, Md.

Insertion of DNA encoding human HCV protease into a vector is easily accomplished when the termini of both the DNA and the vector comprise the same restriction site. If this is not the case, it may be necessary to modify the termini of the DNA and/or vector by digesting back single-stranded DNA overhangs generated by restriction endonuclease cleavage to produce blunt ends, or to achieve the same result by filling in the single-stranded termini with an appropriate DNA polymerase. Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing.

Many *E. coli*-compatible expression vectors can be used to produce soluble HCV NS3 protease of the present invention, including but not limited to vectors containing bacterial or bacteriophage promoters such as the Tac, Lac, Trp, Lac UV5, 1 $P_r$ and 1 $P_L$ promoters. Preferably, a vector selected will have expression control sequences that permit regulation of the rate of HCV protease expression. Then, HCV protease production can be regulated to avoid overproduction that could prove toxic to the host cells. Most preferred is a vector comprising, from 5' to 3' (upstream to downstream), a Tac promoter, a lac $I^q$ repressor gene and DNA encoding mature human HCV protease. The vectors chosen for use in this invention may also encode secretory leaders such as the ompA or protein A leader, as long as such leaders are cleaved during post-translational processing to produce mature HCV protease or if the leaders are not cleaved, the leaders do not interfere with the enzymatic activity of the protease.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology*, Greene and Wiley, NY. Techniques for synthesis of polypeptides are described, e.g., in Merrifield (1963) *J. Amer. Chem. Soc.* 85:2149–2156; Merrifield (1986) *Science* 232: 341–347; and Stewart et al (1984)., *"Solid Phase Peptide Synthesis"* (2nd Edition), Pierce Chemical Co., Rockford, Ill.; and Atherton, et al. (1989) *Solid Phase Peptide Synthesis: A Practical Approach*, IRL Press, Oxford; and Grant (1992) *Synthetic Peptides: A User's Guide*, W. H. Freeman, NY.

The smaller peptides such as the NS4A cofactor, SEQ ID NO: 6, 7 and 8, and the substrates 5A/5B, SEQ ID NO: 5, and 4B/5A, SEQ ID NO: 9 can be synthesized by a suitable method such as by exclusive solid phase synthesis, partial solid phase methods, fragment condensation or classical solution synthesis. The polypeptides are preferably prepared by solid phase peptide synthesis as described by Merrifield, J. Am. Chem. Soc. 85:2149 (1963). The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexyloxycarbonyl] and alkyl type protecting groups (e.g., benzyl, triphenylmethyl). The preferred protecting groups are tBoc and Fmoc, thus the peptides are said to be synthesized by tBoc and Fmoc chemistry, respectively.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide. In tBoc chemistry, the side-chain protecting groups for trifunctional amino acids are mostly benzyl based. In Fmoc chemistry, they are mostly tert.-butyl or trityl based.

In tBoc chemistry, the preferred side-chain protecting groups are tosyl for Arg, cyclohexyl for Asp, 4-methylbenzyl (and acetamidomethyl) for Cys, benzyl for Glu, Ser and Thr, benzyloxymethyl (and dinitrophenyl) for His, 2-Cl-benzyloxycarbonyl for Lys, formyl for Trp and 2-bromobenzyl for Tyr. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for Arg, trityl for Asn, Cys, Gln and His, tert. butyl for Asp, Glu, Ser, Thr and Tyr, tBoc for Lys and Trp.

For the synthesis of phosphopeptides, either direct or post-assembly incorporation of the phosphate group is used. In the direct incorporation strategy, the phosphate group on Ser, Thr or Tyr may be protected by methyl, benzyl or tert.butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl group of Ser, Thr or Tyr was derivatized on solid phase with di-tert.butyl-, dibenzyl- or dimethyl-N,N'-diisopropylphosphoramidite and then oxidized by tert.butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) is used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al (1984)., *"Solid Phase Peptide Synthesis"* (2nd Edition), Pierce Chemical Co., Rockford, Ill.; and Bayer & Rapp (1986) *Chem. Pept. Prot.* 3, 3; and Atherton, et al. (1989) *Solid Phase Peptide Synthesis: A Practical Approach*, IRL Press, Oxford.

The C-terminal amino acid, protected at the side-chain if necessary and at the alpha-amino group, is attached to a hydroxylmethyl resin using various activating agents including dicydohexylcarbodiimide (DCC), N,N'-diisopropylcarbodiimide DIPCDI), and carbonyldiimidazole (CDI). It can be attached to chloromethyl or chlorotrityl resin directly in its cesium tetramethylammonium salt form or in the presence of triethylamine (TEA) or diisopropyl-ethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions inducting DCC, DIPCDI, 2-chloro-1,3-dimethylimidium hexafluorophosphate (CIP), benzotriazol-1-yl-oxy-tris-(dimethylamino)-phosphonium hexafluorophosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyluronium hexafluorophosphate (HBTU) and its tetrafluoroborate analog (TBTU) or its pyrrolidine analog (HBPyU), O-(7-azabenzotriazol-1-yl)-1,1,3,3-tetramethyluronium hexafluorophosphate (HATU) and its tetrafluoroborate analog (TATU) or pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidine (NMP) or in DMF, $CH_2Cl_2$ or mixtures thereof. The extent of completion of the coupling reaction can be monitored at each stage, e.g., by the ninhydrin reaction as described by Kaiser et al., *Anal. Biochem.* 34:595 (1970). In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired polypeptide, the polypeptide-resin is cleaved with a reagent with proper scavengers. The Fmoc peptides are usually cleaved and deprotected by TFA with scavengers (e.g., $H_2O$, ethanedithiol, phenol and thioanisole). The tBoc peptides are usually cleaved and deprotected with liquid HF for 1–2 hours at $-5°$ to $0°$ C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of Trp and dinitrophenyl group of His need to be removed, respectively, by piperidine and thiophenol in DMF prior to the HF cleavage. The acetamidomethyl group of Cys can be removed by mercury(II) acetate and alternatively by iodine, thallium (III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

The following examples are included to illustrate the present invention but not to limit it.

EXAMPLE 1

Production of HCV NS3 Protease

A. Plasmid constructions.

Figure 2:
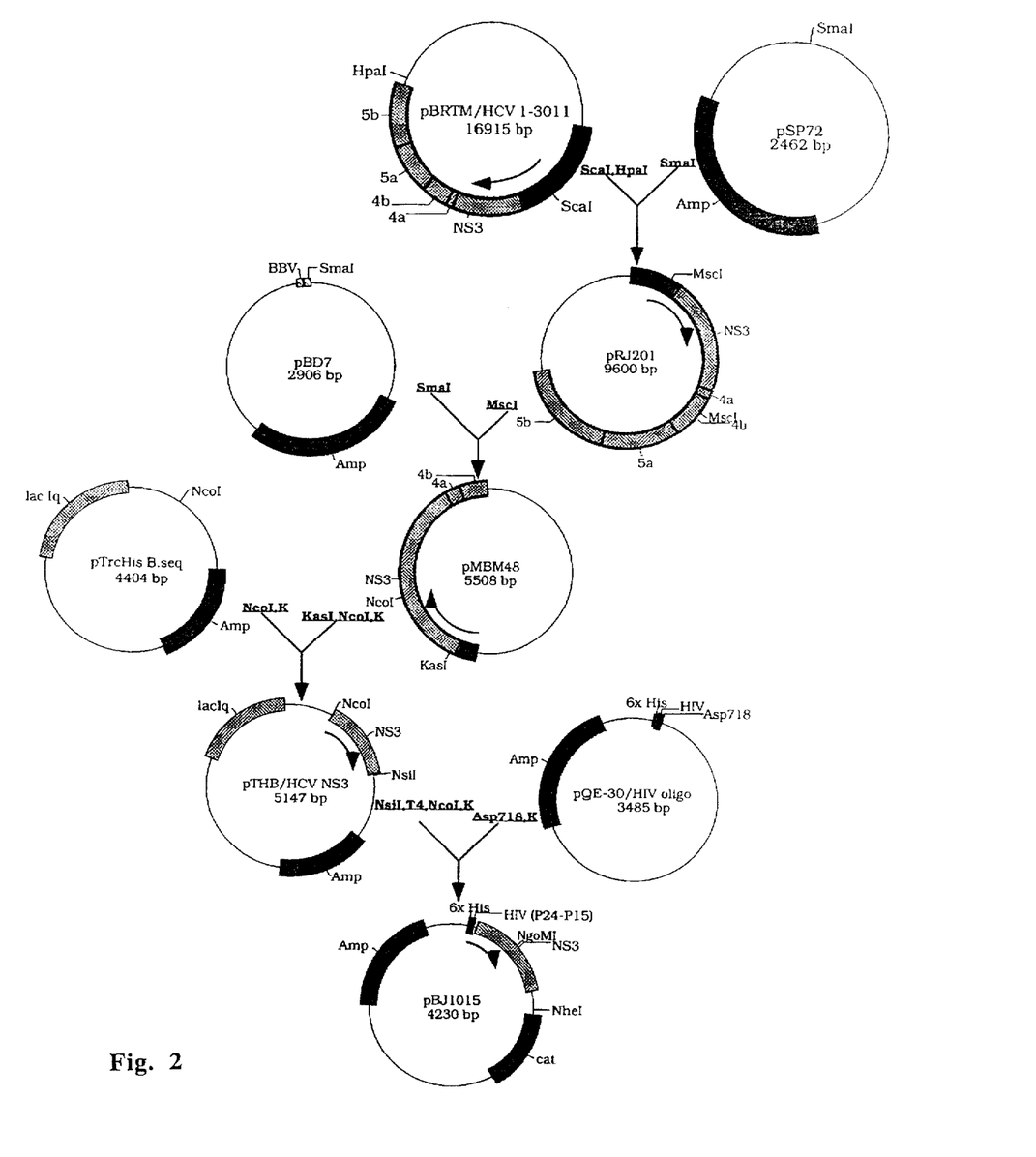
FIG. 2 depicts the recombinant synthesis of plasmid pBJ1015.
Figure 3:
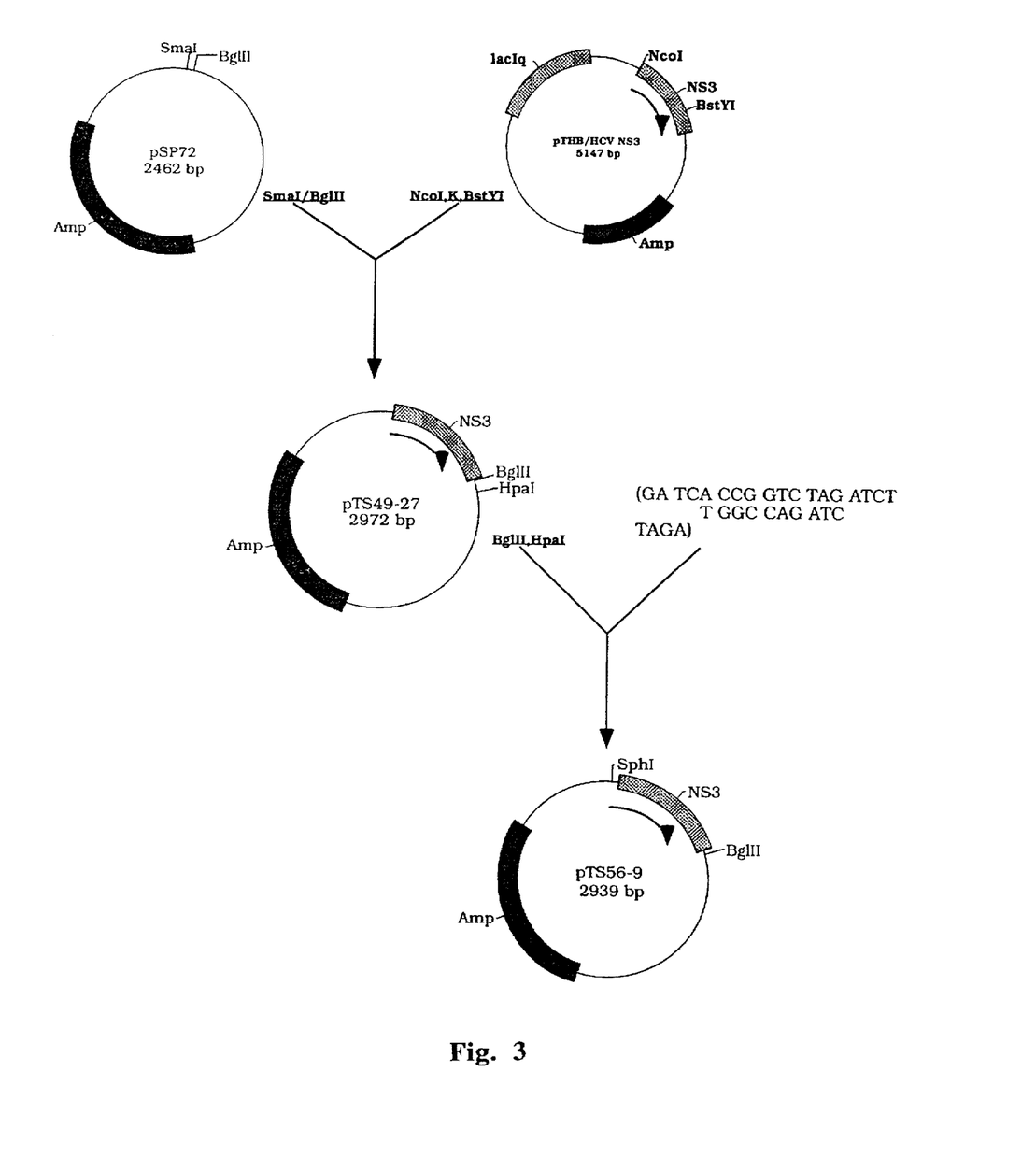
FIG. 3 depicts the recombinant synthesis of plasmid pTS56-9.

Several plasmids were designed and constructed using standard recombinant DNA techniques (Sambrook, Fritsch & Maniatis) to express the HCV protease in *E. coli* (FIGS. 2–7). All HCV specific sequences originated from the parental plasmid pBRTM/HCV 1-3011 (Grakoui et al. 1993). To express the N-terminal 183 amino acid versions of the protease, a stop codon was inserted into the HCV genome using synthetic oligonucleotides (FIG. 3). The plasmids designed to express the N-terminal 246 amino acid residues were generated by the natural Nco1 restriction site at the C-terminus.

i) Construction of the plasmid pBJ1015 (FIG. 2)

The plasmid pBRTM/HCV 1-3011 containing the entire HCV genome (Grakoui A., et al, *J. Virol.* 67: 1385–1395) was digested with the restriction enzymes Sca I and Hpa I and the 7138 bp (base pair) DNA fragment was isolated and cloned to the Sma I site of pSP72 (Promega) to produce the plasmid, pRJ201. The plasmid pRJ 201 was digested with Msc I and the 2106 bp Msc I fragment was isolated and cloned into the Sma I site of the plasmid pBD7. The resulting plasmid pMBM48 was digested with Kas I and Nco I, and the 734 bp DNA fragment after blunt ending with Klenow polymerase was isolated and cloned into Nco I digested, klenow polymerase treated pTrc HIS B seq expression plasmid (Invitrogen). The ligation regenerated a Nco I site at the 5' end and Nsi I site at the 3' end of HCV sequence. The plasmid pTHB HCV NS3 was then digested with Nco I and Nsi I, and treated with klenow polymerase and T4 DNA polymerase, to produce a blunt ended 738 bp DNA fragment which was isolated and cloned into Asp I cut, klenow polymerase treated expression plasmid pQE30 (HIV). The resulting plasmid pBJ 1015 expresses HCV NS3 (246 amino acids) protease.

(ii) Construction of the plasmid pTS 56-9 with a stop codon after amino acid 183 (FIG. 3)

The plasmid pTHB HCV NS3 was digested with Nco I, treated with klenow polymerase, then digested with Bst Y I; and the DNA fragment containing HCV sequence was isolated and cloned into Sma I and Bgl II digested pSP72. The resulting plasmid pTS 49-27 was then digested with Bgl II and Hpa I and ligated with a double stranded oligonucleotide:

GA TCA CCG GTC TAG ATCT

T GGC CAG ATC TAGA (SEQ ID NO 3) to produce pTS 56-9. Thus, a stop codon was placed directly at the end of DNA encoding the protease catalytic domain of the NS3 protein. This enabled the HCV protease to be expressed independently from the helicase domain of the NS3 protein.

Figure 4:
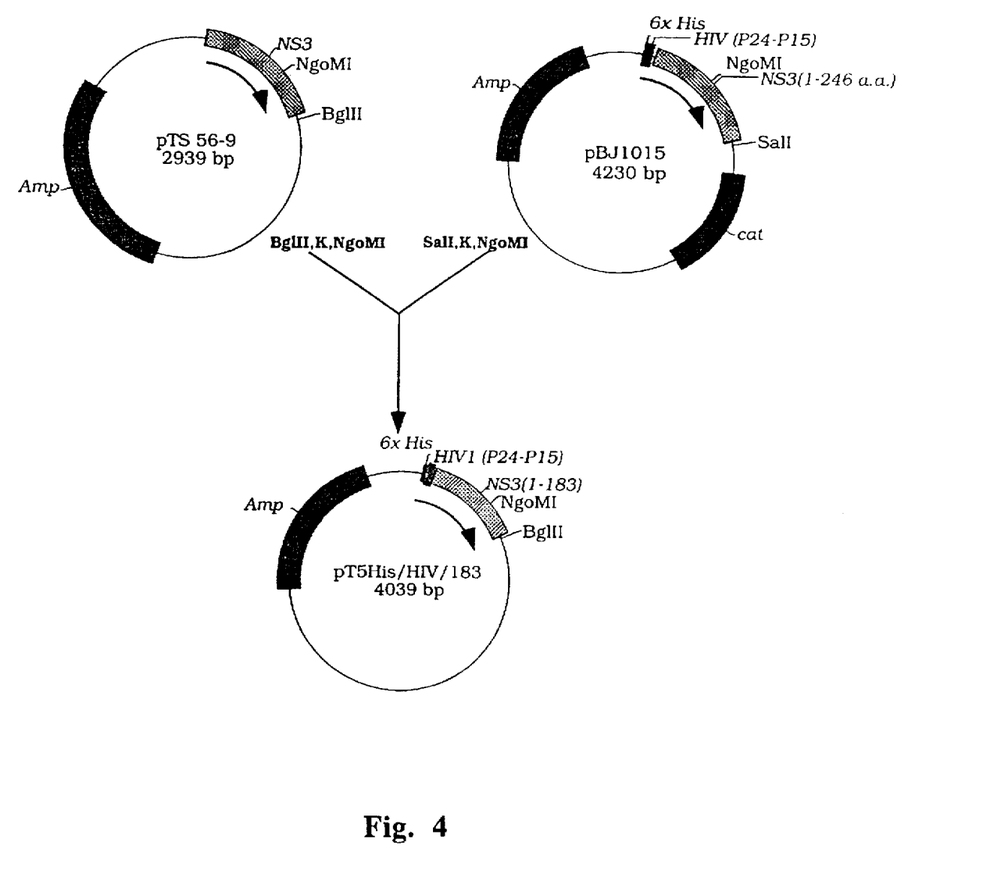
FIG. 4 depicts the recombinant synthesis of plasmid pT5His/HIV/183.

(iii) Construction of the plasmid pT5 His HIV-NS3 (FIG. 4)

The plasmid pTS56-9 was digested with Bgl II, and treated with Klenow polymerase to fill in 5' ends. The plasmid was then digested with NgoM I and the blunt ended Bgl II/NgoMI fragment containing the NS3 sequence was isolated and ligated to the SglII, Klenow treated NgmMI cut and Sal I klenowed pBJ 1015. The resulting plasmid is designated pT5His HIV 183.

EXAMPLE 2

Refolding of Insoluble HCV NS3 Protease

The present example describes a novel process for the refolding of HCV NS3 protease which does not have a solubilizing motif from an *E. coli* inclusion body pellet. This procedure can be used to generate purified enzyme for activity assays and structural studies.

Extraction and Purification of His-HIV 183 from the *E. coli* inclusion body pellet

*E. coli* cells harboring the plasmid for HisHIV183 were used to transform a culture of *E. coli* strain M15 [pREP] (Qiagen), which over-expresses the lac repressor, according to methods recommended by commercial source. M15 [pREP] bacteria harboring recombinant plasmids were grown overnight in 20-10-5 broth supplemented with 100 µg/ml ampicillin and 25 µg/ml kanamycin. Cultures were diluted to O.D.600 of 0.1, then grown at 37° C. to O.D.600 of 0.6 to 0.8, after which IPTG was added to a final concentration of 1 mM. At 2 to 3 hours post-induction, the cells were harvested by pelleting, and the cell pellets were washed with 100 mM Tris, pH 7.5, and pelleted by centrifugation. The cell pellet was resuspended in 10 ml of 0.1M Tris-HCl, 5 mM EDTA, pH 8.0 (Buffer A) for each gm wet weight of pellet. The pellet was homogenized and resuspended using a Dounce homogenizer. The suspension was clarified by centrifugation at 20,000×g for 30 minutes at 4° C. The pellet was sequentially washed with the following five buffers:
1. Buffer A
2. 1.0M sodium chloride (NaCl) in buffer A
3. 1.0% Triton X-100 in buffer A
4. Buffer A
5. 1.0M Guanidine HCl (GuHCl) in buffer A.

The washed pellet was solubilized with 5M GuHCl, 1% beta mercaptoethanol in buffer A (3 ml per gm wet wt. of pellet) using a Dounce homogenizer and centrifuged at 100,000×g for 30 minutes at 4° C. Purification of denatured HisHIV183 from high molecular weight aggregates was accomplished by size exclusion on a SEPHACRYL S-300 gel filtration column.

In particular, an 8 ml sample of the 5.0M GuHCl *E. coli* extract was applied to a 160 ml Pharmacia S-300 column (1.6×100 cm) at a flow rate of 1.0 ml/min. The column buffer was comprised of 5.0M GuHCl, 0.1M Tris-HCl, pH 8.0, and 5.0 mM EDTA. The fraction she was 5.0 ml. Appropriate fractions were pooled based on the results of SDS-PAGE, as well as N-terminal sequence analysis of the protein transferred to a Pro-Blot.

Detergent-assisted refolding of HCV-protease

The protein was concentrated by ultrafiltration using a 43 mm Amicon YM10 membrane to 1.0 mg per ml in 5M GuHCl, 0.1M Tris-HCl pH 8.0, 1.0 mM EDTA, 1.0% beta-mercaptoethanol. It was then diluted 50-fold to 0.1M GuHCl in refolding buffer (100 mM sodium phosphate pH 8.0, 10 mM DTT, 0.1% lauryl maltoside) and the mixture was incubated on ice for at least one hour. A 25 ml sample containing 500 µg of the protein in the refolding buffer was applied to a Pro-RPC HR 3/5 reversed phase chromatography column. The applied sample contained 500 µg protein in 25 ml of refolding buffer. To the column was then applied a solution B comprised of 99.9% $H_2O$+0.1% trifluoroacetic acid (TFA). A 10 ml volume of solution C [10% $H_2O$, 90% acetonitrile (AcN)+0.1% TFA] was applied to the column at a 0–60% gradient into solution B at a flow rate of 0.5 ml/min, and a fraction size of 0.5 ml. The fractions were monitored at A214; 2.0 absorbance units full scale (AUFS).

Fractions containing the protein (corresponding to peak 1) were pooled for renaturation by stepwise dialysis. The fractions were first dialysed in 0.1% TFA in 25% glycerol overnight at 4° C. These pooled fractions had a concentration of 0.1% TFA, 40% acetonitrile and a pH of less than 1. The fractions were then dialyzed in 0.01% TFA in 25% glycerol overnight at 4° C. raising the pH to about 2; then dialyzed in 0.001% TFA in 25% glycerol for 3.0 hours raising the pH to about 3; then dialyzed for 3 hours at 4° C. in 50 mM $NaPO_4$, pH 6.0, 10 mM DTT in 25% glycerol raising the pH to about 6. The protein was then dialyzed for 3.0 hours at 4° C. in 50 mM $NaPO_4$, pH 7.0, 0.15M NaCl, 10 mM DTT in 25% glycerol; and then finally dialyzed in 50 mM $NaPO_4$, pH 7.8, 0.3M NaCl, 10 mM DTT, 0.2% Tween 20 in 25% glycerol. This resulted in purified, refolded, soluble, active HCV NS3 protease resulting in a solution having a pH of about 7.4–7.8.

Far UV circular dichroism (CD) analysis of the protein was used to monitor the refolding from an acid denatured state to a folded state at neutral pH. The protein recovery was monitored by a UV scan and SDS-PAGE analysis.
Results:

Detergent-assisted Refolding of His-HIV183

HisHIV183 was quantitatively extracted from an *E. coli* inclusion body pellet. SDS-PAGE analysis at the various stages of extraction shows that sequential washes are essential to remove significant amounts of the contaminating proteins. HisHIV183 was extracted from the washed inclusion body pellet in the presence of 5M GuHCl. The 5M GuHCl extract was applied to a SEPHACRYL S-300 column and the appropriate fractions were pooled based on SDS-PAGE analysis. The amino acid sequence of the first ten residues was verified.

Refolding was performed at very low concentrations of protein, in the presence of DTT, lauryl maltoside and glycerol at 4° C. The diluted protein was concentrated on a Pro-RPC reversed phase column. Two peaks were obtained based on the UV and protein profile. Only Peak 1 has yielded soluble protein after stepwise dialysis. Far UV CD spectral analysis was used to monitor refolding from a denatured state at acid pH to a folded state at neutral pH. At pH 7.4, the protein was found to exhibit significant amounts of secondary structure that is consistent with that of beta sheet protein. At low pH, the CD spectrum showed that it is fully random coil, having a minimal molar ellipticity at 200 nm. The ratio of this minimum at 200 nm to that of the shoulder at 220 nm is approximately 4:1. This ratio decreased when the secondary structure formation occurred at neutral pH.

A UV scan at each step of dialysis showed that the protein recovery was >90% up to pH 7.0 and that there was no light scattering effect due to protein aggregates. SDS-PAGE analysis also indicated that there was no loss of protein up to pH 7.0 during refolding. Precipitation of protein occurred at the last step of dialysis, and the soluble protein was clarified by centrifugation. The overall protein recovery was about 10%. The refolded protein was found to be active in a trans-cleavage assay using the in vitro-translated 5A/5B substrate in the presence of 4A peptide.

EXAMPLE 3

Analysis of NS3 Protease Activity By In Vitro Translation Assay

To detect HCV NS3 protease activity in trans, we have expressed a 40 kD protein containing the NS5A/5B cleavage site in cell-free translation system and used that as the substrate for the enzyme. The substrate protein produces two protein products of apparent molecular weight 12.5 kD (NS 5A') and 27 kD (NS5B') upon cleavage by the HCV NS3 protease.

The plasmid pTS102 encoding the substrate 5A/5B was linearized by digestion with EcoR I and was transcribed using T7 RNA polymerase in vitro. The RNA was translated in presence of $^{35}S$ methionine in rabbit reticulocyte lysates according to the manufacturer's (Promega) protocol to produce HCV specific protein. In a 20 µl total reaction mixture containing 10 mM Tris, pH 7.5, 1 mM DTT, 0.5 mM EDTA, and 10% glycerol was placed 2 to 8 µl of $^{35}S$ methionine-labeled translated 5A/5B substrate. The reaction was started with the addition of 10 µl of HCV NS3 protease (SEQ ID NO: 2) with an approximately equimolar amount (2 µM) of the carboxyterminal 33 mer cofactor NS4A (SEQ ID NO: 7) in solubilization buffer (50 mM Na Phosphate, pH 7.8, 0.3M NaCl, 0.2% Tween 20, 10 mM DTT or BME, 10% glycerol), and incubated at 30° C. for about one hour. Reactions were stopped by adding an equal volume of 2X Laemmli sample buffer (Enprotech Inc.) and heating at 100° C. for 3 minutes. Reaction products were separated by SDS PAGE electrophoresis; gels were fixed, dried and subjected to autoradiography.

The assay was able to cleave 5A/5B substrate in a dose responsive manner, produring the expected cleaved products: 5A (12.5 kD) and 5B (27 kD) as shown by SDS PAGE analysis. The production of cleaved 5A and 5B polypeptides from the 5A/5B substrate is proof that soluble, active, refolded HCV protease was indeed produced by the process of the present invention.

EXAMPLE 4

Detergent-Assisted Refolding of the Catalytic Domain, His-HIV 183

HCV protease catalytic domain has been expressed in high concentrations in E. coli as an inclusion body pellet and is amenable to refolding studies. His-HIVNS3183 contains a six-residue polyhistidine tag, a 27 residue HIV protease cleavage sequence and a serine protease domain of 183 amino acids. His-HIVNS3 183 was extracted with 5M GuHCL according to the procedure of Example 2. A sample of the 5.0M GuHCl E. coli extract was applied to a 500 ml Pharmacia S-300 column (5.0×100 cm) at a flow rate of 4 ml/min. The column buffer was the same buffer used in Example 2. About 100 mg of highly purified protein was obtained for refolding studies.

The fractions containing the protein (1.0 mg/ml) were collected and diluted 50-fold in buffer A (100 mM sodium phosphate pH 7.8, 25% glycerol, 0.1% lauryl maltoside and 10 mM DTT) and immediately applied to a POROS 20R1 reversed phase column. A main peak and a shoulder were eluted with a 0–60% acetonitrile gradient in 0.1% TFA. Only the main peak, not the shoulder, yielded active protease using a stepwise dialysis procedure.

Fractions containing the protein (corresponding to peak 1) were pooled for renaturation by stepwise dialysis. The fractions were first dialysed in 0.1% TFA in 25% glycerol overnight at 4° C. These pooled fractions had a concentration of 0.1% TFA, 40% acetonitrile and a pH of less than 1. The fractions were then dialyzed in 0.01% TFA in 25% glycerol overnight at 4° C. raising the pH to about 2; then dialyzed in 0.001% TFA in 25% glycerol for 3.0 hours raising the pH to about 3; then dialyzed for 3 hours at 4° C. in 50 mM NaPO$_4$, pH 6.0, 10 mM DTT in 25% glycerol raising the pH to about 6. The protein was then dialyzed for 3.0 hours at 4° C. in 50 mM NaPO$_4$, pH 7.0, 0.15M NaCl, 10 mM DTT in 25% glycerol; and then finally dialyzed in 50 mM NaPO$_4$, pH 7.8, 0.3M NaCl, 10 mM DTT, in 25% glycerol. This resulted in purified, refolded, soluble, active HCV NS3 protease resulting in a solution having a pH of about 7.4–7.8. This resulted in an approximate 27% yield of active protease (>95% purity).

The refolded protein was found to be active in the presence of a NS4A peptide (33-mer) in the in vitro-translation assay using a truncated 5A-5B substrate. Three small scale refolding experiments (1.0 & 10.0 and 20 mg) gave reproducible yields (30%) of active soluble protease. We performed a loading study on the reverse phase column to improve the recovery of refolded protein. A 2.5 mg scale refolding gave 27% recovery of active protease. Refolding of HCV protease from a one liter fermentation is estimated to give 4–5 mg of active protein.

We have studied the enhancement activity of NS4A peptides on the activity of refolded HCV protease in the SPA assay. Kinetics of this enzyme has been determined with the unlabeled peptide in the HPLC assay. (Table)

Table Kinetics of Refolded HCV Protease Catalytic Domain Determined in the presence of NS4A (22–54)

Non-Linear Regression

Km=63.626+/−19.834 µM

Vmax=22.9+/−3.397 pmoles/min/0.5 µg enzyme $k_{cat}$=1.05 min$^{-1}$ $k_{cat}$/Km=264.7M$^{-1}$s$^{-1}$ Preliminary Detergent-Assisted Refolding of NS3 631

The full-length HCV protease NS3 631 was extracted from an E. coli inclusion body pellet and purified using Sephacryl S-300 chromatography. Forty milligrams of highly purified NS3 631 has been obtained from a six liter fermentation. This protein migrated as a doublet on SDS-PAGE under reducing conditions. N-terminal sequencing of the two immunoreactive bands indicated that the majority of the protein has a blocked N-terminus. The biochemical basis for the heterogeneity is unknown. Using modified detergent-assisted refolding scheme that was described for HisHIV183, low amounts of soluble protein was obtained. The procedure was modified by including 0.5M arginine hydrochloride in the refolding buffer. The refolded protein showed activity in the presence of NS4A peptide in the in vitro-translation assay using truncated 5A-5B as a substrate.

---

We claim:

1. A process for producing soluble, proteolytically active, refolded Hepatitis C Virus NS3 protease (HCV NS3 protease) from insoluble, recombinantly produced HCV NS3 protease aggregates comprising:

(a) extracting insoluble, aggregates of HCV NS3 protease from bacteria producing said aggregates;

(b) solubilizing the aggregates of said HCV NS3 protease in a buffer containing a denaturing reagent;

(c) placing said solubilized HCV NS3 protease from step (b) in a buffer containing a reducing agent, said buffer having an acidic pH;

(d) removing said denaturing reagent from said buffer under conditions wherein said buffer maintains an acidic pH; and (e) raising said pH of said buffer containing said HCV NS3 protease in a stepwise manner to a pH of about 7–8 so as to produce properly refolded soluble, active HCV NS3 protease.

2. The process of claim 1 wherein the denaturing reagent is guanidine hydrochloride (GuHCl).

3. The process of claim 2 wherein the solution of GuHCl contains GuHCl at a concentration of about 5M.

4. The process of claim 1 wherein the reducing agent is dithiothreitol or β-mercaptoethanol.

5. The process of claim 1 wherein the buffer containing the reducing agent also contains a non-ionic detergent.

6. The process of claim 5 wherein the non-ionic detergent is selected from the group consisting of lauryl maltoside, polyoxyethylene ethers, polyoxyethylene 9-lauryl ethers and octylglucoside.

7. The process of claim 6 wherein the solubilized protease of step (c) is in a 5M GuHCl solution containing about 10 mM DTT and 0.1% lauryl maltoside.

8. The process of claim 1 wherein step (d) comprises applying the buffer containing the solubilized protease of step (c) to a reverse phase chromatography column under conditions wherein fractions collected have an acidic pH.

9. The process of claim 8 comprising the additional steps of eluting the column with a 0%–60% acetonitrile gradient and collecting fractions having an acidic pH.

10. The process of claim 9 wherein said gradient further comprises about 0.1% TFA.

11. The process of claim 8 wherein after the buffer containing the protease of step (c) is applied to the reverse phase chromatography column, said column is eluted with a first solution comprising about 99.9% $H_2O$ and about 0.1% triflouroacetic acid (TFA) and a second solution comprising about 10% $H_2O$ and about 90% acetonitrile and about 0.1% TFA, said first and second solutions being added to said column by a 0–60% gradient of said second solution.

12. The process of claim 11 further comprising dialyzing the fractions containing the solubilized protease of step (d) first in an aqueous solution of 0.1% TFA resulting in a solution having a pH less than 1, then dialyzing the fraction in an aqueous solution of 0.01% TFA resulting in a solution having a pH of about 2 and then dialyzing the fractions in 0.001% TFA resulting in a solution having a pH of about 3, then dialyzing the solution in an aqueous solution having a pH of about 6, then dialysing the solution in an aqueous solution having a pH of about 7, then dialysing the solution in an aqueous solution having a pH of about 7.8 resulting in a solution having a pH of 7.4–7.8 containing properly refolded active HCV NS3 protease.

\* \* \* \* \*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 549 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: HCV NS3 Protease ( x i ) SEQUENCE DESCRIPTION: SEQ ID NO: 1:

-continued

| | | | | | | | | | | | | | | | |
|---|---|---|---|---|---|---|---|---|---|---|---|---|---|---|---|
| GCG | CCC | ATC | ACG | GCG | TAC | GCC | CAG | CAG | ACG | AGA | GGC | CTC | CTA | GGG | 45 |
| Ala | Pro | Ile | Thr | Ala | Tyr | Ala | Gln | Gln | Thr | Arg | Gly | Leu | Leu | Gly | |
| 1 | | | | 5 | | | | | 10 | | | | | 15 | |
| TGT | ATA | ATC | ACC | AGC | CTG | ACT | GGC | CGG | GAC | AAA | AAC | CAA | GTG | GAG | 90 |
| Cys | Ile | Ile | Thr | Ser | Leu | Thr | Gly | Arg | Asp | Lys | Asn | Gln | Val | Glu | |
| | | | | 20 | | | | | 25 | | | | | 30 | |
| GGT | GAG | GTC | CAG | ATC | GTG | TCA | ACT | GCT | ACC | CAA | ACC | TTC | CTG | GCA | 135 |
| Gly | Glu | Val | Gln | Ile | Val | Ser | Thr | Ala | Thr | Gln | Thr | Phe | Leu | Ala | |
| | | | | 35 | | | | | 40 | | | | | 45 | |
| ACG | TGC | ATC | AAT | GGG | GTA | TGC | TGG | ACT | GTC | TAC | CAC | GGG | GCC | GGA | 180 |
| Thr | Cys | Ile | Asn | Gly | Val | Cys | Trp | Thr | Val | Tyr | His | Gly | Ala | Gly | |
| | | | | 50 | | | | | 55 | | | | | 60 | |
| ACG | AGG | ACC | ATC | GCA | TCA | CCC | AAG | GGT | CCT | GTC | ATC | CAG | ATG | TAT | 225 |
| Thr | Arg | Thr | Ile | Ala | Ser | Pro | Lys | Gly | Pro | Val | Ile | Gln | Met | Tyr | |
| | | | | 65 | | | | | 70 | | | | | 75 | |
| ACC | AAT | GTG | GAC | CAA | GAC | CTT | GTG | GGC | TGG | CCC | GCT | CCT | CAA | GGT | 270 |
| Thr | Asn | Val | Asp | Gln | Asp | Leu | Val | Gly | Trp | Pro | Ala | Pro | Gln | Gly | |
| | | | | 80 | | | | | 85 | | | | | 90 | |
| TCC | CGC | TCA | TTG | ACA | CCC | TGC | ACC | TGC | GGC | TCC | TCG | GAC | CTT | TAC | 315 |
| Ser | Arg | Ser | Leu | Thr | Pro | Cys | Thr | Cys | Gly | Ser | Ser | Asp | Leu | Tyr | |
| | | | | 95 | | | | | 100 | | | | | 105 | |
| CTG | GTT | ACG | AGG | CAC | GCC | GAC | GTC | ATT | CCC | GTG | CGC | CGG | CGA | GGT | 360 |
| Leu | Val | Thr | Arg | His | Ala | Asp | Val | Ile | Pro | Val | Arg | Arg | Arg | Gly | |
| | | | | 110 | | | | | 115 | | | | | 120 | |
| GAT | AGC | AGG | GGT | AGC | CTG | CTT | TCG | CCC | CGG | CCC | ATT | TCC | TAC | CTA | 405 |
| Asp | Ser | Arg | Gly | Ser | Leu | Leu | Ser | Pro | Arg | Pro | Ile | Ser | Tyr | Leu | |
| | | | | 125 | | | | | 130 | | | | | 135 | |
| AAA | GGC | TCC | TCG | GGG | GGT | CCG | CTG | TTG | TGC | CCC | GCG | GGA | CAC | GCC | 450 |
| Lys | Gly | Ser | Ser | Gly | Gly | Pro | Leu | Leu | Cys | Pro | Ala | Gly | His | Ala | |
| | | | | 140 | | | | | 145 | | | | | 150 | |
| GTG | GGC | CTA | TTC | AGG | GCC | GCG | GTG | TGC | ACC | CGT | GGA | GTG | ACC | AAG | 495 |
| Val | Gly | Leu | Phe | Arg | Ala | Ala | Val | Cys | Thr | Arg | Gly | Val | Thr | Lys | |
| | | | | 155 | | | | | 160 | | | | | 165 | |
| GCG | GTG | GAC | TTT | ATC | CCT | GTG | GAG | AAC | CTA | GAG | ACA | ACC | ATG | AGA | 540 |
| Ala | Val | Asp | Phe | Ile | Pro | Val | Glu | Asn | Leu | Glu | Thr | Thr | Met | Arg | |
| | | | | 170 | | | | | 175 | | | | | 180 | |
| TCC | CCG | GTG | | | | | | | | | | | | | 549 |
| Ser | Pro | Val | | | | | | | | | | | | | |

( 2 ) INFORMATION FOR SEQ ID NO:2:

( i ) SEQUENCE CHARACTERISTICS:
        ( A ) LENGTH: 630 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: pT5His/HIV/183

( x i ) SEQUENCE DESCRIPTION: SEQ ID NO: 2:

| | | | | | | | | | | | | | | | |
|---|---|---|---|---|---|---|---|---|---|---|---|---|---|---|---|
| ATG | AGA | GGA | TCG | CAT | CAC | CAT | CAC | CAT | CAC | GGA | TCC | CAT | AAG | GCA | 45 |
| Met | Arg | Gly | Ser | His | His | His | His | His | His | Gly | Ser | His | Lys | Ala | |
| 1 | | | | 5 | | | | | 10 | | | | | 15 | |
| AGA | GTT | TTG | GCT | GAA | GCA | ATG | AGC | CAT | GGT | ACC | ATG | GCG | CCC | ATC | 90 |
| Arg | Val | Leu | Ala | Glu | Ala | Met | Ser | His | Gly | Thr | Met | Ala | Pro | Ile | |
| | | | | 20 | | | | | 25 | | | | | 30 | |
| ACG | GCG | TAC | GCC | CAG | CAG | ACG | AGA | GGC | CTC | CTA | GGG | TGT | ATA | ATC | 135 |
| Thr | Ala | Tyr | Ala | Gln | Gln | Thr | Arg | Gly | Leu | Leu | Gly | Cys | Ile | Ile | |
| | | | | 35 | | | | | 40 | | | | | 45 | |
| ACC | AGC | CTG | ACT | GGC | CGG | GAC | AAA | AAC | CAA | GTG | GAG | GGT | GAG | GTC | 180 |
| Thr | Ser | Leu | Thr | Gly | Arg | Asp | Lys | Asn | Gln | Val | Glu | Gly | Glu | Val | |

-continued

| | | | | | | | | | | | | | | |
|---|---|---|---|---|---|---|---|---|---|---|---|---|---|---|
| Thr | Ser | Leu | Thr | Gly<br>50 | Arg | Asp | Lys | Asn | Gln<br>55 | Val | Glu | Gly | Glu | Val<br>60 |

```
CAG  ATC  GTG  TCA  ACT  GCT  ACC  CAA  ACC  TTC  CTG  GCA  ACG  TGC  ATC        225
Gln  Ile  Val  Ser  Thr  Ala  Thr  Gln  Thr  Phe  Leu  Ala  Thr  Cys  Ile
               65                      70                           75

AAT  GGG  GTA  TGC  TGG  ACT  GTC  TAC  CAC  GGG  GCC  GGA  ACG  AGG  ACC        270
Asn  Gly  Val  Cys  Trp  Thr  Val  Tyr  His  Gly  Ala  Gly  Thr  Arg  Thr
               80                      85                           90

ATC  GCA  TCA  CCC  AAG  GGT  CCT  GTC  ATC  CAG  ATG  TAT  ACC  AAT  GTG        315
Ile  Ala  Ser  Pro  Lys  Gly  Pro  Val  Ile  Gln  Met  Tyr  Thr  Asn  Val
               95                      100                          105

GAC  CAA  GAC  CTT  GTG  GGC  TGG  CCC  GCT  CCT  CAA  GGT  TCC  CGC  TCA        360
Asp  Gln  Asp  Leu  Val  Gly  Trp  Pro  Ala  Pro  Gln  Gly  Ser  Arg  Ser
               110                     115                          120

TTG  ACA  CCC  TGC  ACC  TGC  GGC  TCC  TCG  GAC  CTT  TAC  CTG  GTT  ACG        405
Leu  Thr  Pro  Cys  Thr  Cys  Gly  Ser  Ser  Asp  Leu  Tyr  Leu  Val  Thr
               125                     130                          135

AGG  CAC  GCC  GAC  GTC  ATT  CCC  GTG  CGC  CGG  CGA  GGT  GAT  AGC  AGG        450
Arg  His  Ala  Asp  Val  Ile  Pro  Val  Arg  Arg  Arg  Gly  Asp  Ser  Arg
               140                     145                          150

GGT  AGC  CTG  CTT  TCG  CCC  CGG  CCC  ATT  TCC  TAC  CTA  AAA  GGC  TCC        495
Gly  Ser  Leu  Leu  Ser  Pro  Arg  Pro  Ile  Ser  Tyr  Leu  Lys  Gly  Ser
               155                     160                          165

TCG  GGG  GGT  CCG  CTG  TTG  TGC  CCC  GCG  GGA  CAC  GCC  GTG  GGC  CTA        540
Ser  Gly  Gly  Pro  Leu  Leu  Cys  Pro  Ala  Gly  His  Ala  Val  Gly  Leu
               170                     175                          180

TTC  AGG  GCC  GCG  GTG  TGC  ACC  CGT  GGA  GTG  ACC  AAG  GCG  GTG  GAC        585
Phe  Arg  Ala  Ala  Val  Cys  Thr  Arg  Gly  Val  Thr  Lys  Ala  Val  Asp
               185                     190                          195

TTT  ATC  CCT  GTG  GAG  AAC  CTA  GAG  ACA  ACC  ATG  AGA  TCC  CCG  GTG        630
Phe  Ile  Pro  Val  Glu  Asn  Leu  Glu  Thr  Thr  Met  Arg  Ser  Pro  Val
               200                     205                          210
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO: 3:

GATCACCGGT CTAGATCT          18

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear     ( i i ) MOLECULE TYPE: polypeptide     ( i x ) FEATURE:
        ( A ) NAME/KEY: histidine tag     ( x i ) SEQUENCE DESCRIPTION: SEQ ID NO: 4:

```
Met  Arg  Gly  Ser  His  His  His  His  His  Thr  Asp  Pro
 1                  5                   10
```

( 2 ) INFORMATION FOR SEQ ID NO:5:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: polypeptide ( i x ) FEATURE:
  ( A ) NAME/KEY: Mutant Soluble 5A/5B Substrate ( x i ) SEQUENCE DESCRIPTION: SEQ ID NO: 5:

```
Asp Thr Glu Asp Val Val Ala Cys Ser Met Ser Tyr Thr Trp Thr
 1               5                  10                 15

Gly Lys
```

( 2 ) INFORMATION FOR SEQ ID NO:6:

( i ) SEQUENCE CHARACTERISTICS:
    ( A ) LENGTH: 162 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: Native NS4A ( x i ) SEQUENCE DESCRIPTION: SEQ ID NO: 6:

```
TCA ACA TGG GTG CTC GTT GGC GGC GTC CTG GCT GCT CTG GCC GCG   45
Ser Thr Trp Val Leu Val Gly Gly Val Leu Ala Ala Leu Ala Ala
 1               5                  10                 15

TAT TGC CTG TCA ACA GGC TGC GTG GTC ATA GTG GGC AGG ATT GTC   90
Tyr Cys Leu Ser Thr Gly Cys Val Val Ile Val Gly Arg Ile Val
                20                  25                 30

TTG TCC GGG AAG CCG GCA ATT ATA CCT GAC AGG GAG GTT CTC TAC  135
Leu Ser Gly Lys Pro Ala Ile Ile Pro Asp Arg Glu Val Leu Tyr
                35                  40                 45

CAG GAG TTC GAT GAG ATG GAA GAG TGC
Gln Glu Phe Asp Glu Met Glu Glu Cys
                50
```

( 2 ) INFORMATION FOR SEQ ID NO:7:

( i ) SEQUENCE CHARACTERISTICS:
    ( A ) LENGTH: 33 amino acid residues
    ( B ) TYPE: amino acid
    ( C ) STRANDEDNESS: single
    ( D ) TOPOLOGY: linear ( i i ) MOLECULE TYPE: polypeptide ( i x ) FEATURE:
    ( A ) NAME/KEY: Carboxl 33 mer of NS4A ( x i ) SEQUENCE DESCRIPTION: SEQ ID NO: 7:

```
Cys Val Val Ile Val Gly Arg Ile Val Leu Ser Gly Lys Pro Ala
 1               5                  10                 15

Ile Ile Pro Asp Arg Glu Val Leu Tyr Gln Glu Phe Asp Glu Met
                20                  25                 30

Glu Glu Cys
```

( 2 ) INFORMATION FOR SEQ ID NO:8:

( i ) SEQUENCE CHARACTERISTICS:
    ( A ) LENGTH: 33 amino acid residues
    ( B ) TYPE: amino acid -continued

```
        ( C ) STRANDEDNESS: single
        ( D ) TOPOLOGY: linear ( i i ) MOLECULE TYPE: polypeptide ( i x ) FEATURE:
            ( A ) NAME/KEY: Carboxl 33 mer of NS4A of HCV-BK strain ( x i ) SEQUENCE DESCRIPTION: SEQ ID NO: 8:

Ser  Val  Val  Ile  Val  Gly  Arg  Ile  Ile  Leu  Ser  Gly  Arg  Pro  Ala
1                   5                        10                       15

Ile  Val  Pro  Asp  Arg  Glu  Leu  Leu  Tyr  Gln  Glu  Phe  Asp  Glu  Met
                    20                       25                       30

Glu  Glu  Cys ( 2 ) INFORMATION FOR SEQ ID NO:9:

( i ) SEQUENCE CHARACTERISTICS:
            ( A ) LENGTH: 20 amino acid residues
            ( B ) TYPE: amino acid
            ( C ) STRANDEDNESS: single
            ( D ) TOPOLOGY: linear ( i i ) MOLECULE TYPE: polypeptide ( i x ) FEATURE:
            ( A ) NAME/KEY: Soluble 4B/5A Substrate ( x i ) SEQUENCE DESCRIPTION: SEQ ID NO: 9:

Trp  Ile  Ser  Ser  Glu  Cys  Thr  Thr  Pro  Cys  Ser  Gly  Ser  Trp  Leu
1                   5                        10                       15

Arg  Asp  Ile  Trp  Asp
                    20
```